United States Patent [19]

Aoki et al.

[11] Patent Number: 4,936,841

[45] Date of Patent: Jun. 26, 1990

[54] FLUID CONTAINER

[75] Inventors: Osamu Aoki, Osaka; Kiyonori Okada; Seizo Sunago, both of Toyonaka; Hitoshi Futagawa, Otsu; Kohji Ikeda; Shuji Hasegawa, both of Osaka, all of Japan

[73] Assignees: Fujisawa Pharmaceutical Co., Ltd.; Nissho Corporation, both of Osaka, Japan

[21] Appl. No.: 326,518

[22] Filed: Mar. 21, 1989

[30] Foreign Application Priority Data

Mar. 31, 1988 [JP] Japan .................................. 63-80497

[51] Int. Cl.$^5$ .............................................. A61B 19/00

[52] U.S. Cl. ...................................... 604/413; 604/82; 604/88; 206/222

[58] Field of Search ................ 604/403, 408, 411, 412, 604/413, 414, 82, 87, 88, 91, 56; 206/219, 222; 141/329, 330

[56] References Cited

U.S. PATENT DOCUMENTS 3,977,555 8/1976 Larson ................................ 215/247
4,244,467 1/1981 Cavazza .............................. 206/222
4,576,211 3/1986 Valentini et al. .................. 141/329
4,583,971 4/1986 Bocquet et al. ....................... 604/82
4,589,879 5/1986 Pearson .............................. 604/411

*Primary Examiner*—Robert A. Hafer
*Assistant Examiner*—Lynda M. Cofsky
*Attorney, Agent, or Firm*—Oblon, Spivak, McClelland, Maier & Neustadt

[57] ABSTRACT

Disclosed is a fluid container having a flexible bag containing a diluent and having a closing film at its upper end, a capsule connected to the flexible bag, a drug container held in the capsule and a communicating member for communicating the flexible bag with the drug container. The communicating member has a double-edged hollow needle having a hub in the midway thereof, and a controlling mechanism for controlling the order of communication in such a manner that the plug of the drug container is stuck with one edge of the needle and thereafter the closing film of the flexible bag is stuck with the other end of the needle. The mixing procedure is sure and simple, and can be carried out in a short period of time.

14 Claims, 16 Drawing Sheets

F/G.6
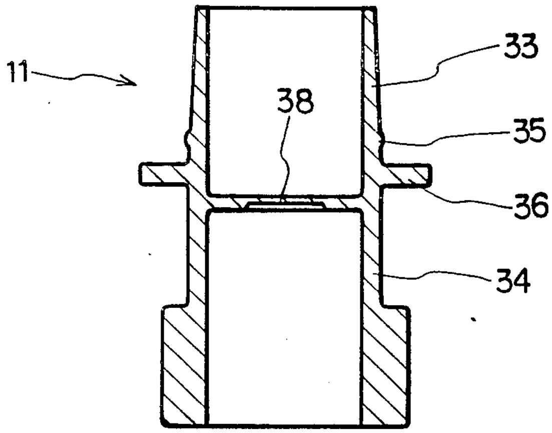
F/G.7
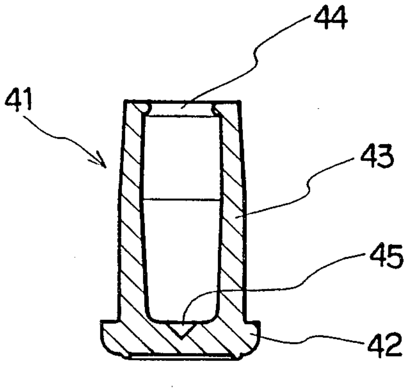

A
A
A
2
3
3
3
4
4
4
6
6
7
7
8
8
11
17
19
20
27
38
41
42
44
44
48
48
48
48
55
56
56
57
57
58

FLUID CONTAINER

BACKGROUND OF THE INVENTION

1. Field of the Invention

The present invention relates to a fluid container used for dripping in the medical field.

2. Discussion of the Background

Hitherto, a powder-filled drug or a freeze-dried drug contained in a container such as a vial is dissolved with a diluent and used as a solution for dripping. In that case, a container containing the above-mentioned drug and a container containing a diluent are connected to each other using a connector such as a double-edged needle or communicating pipe. The diluent is moved into the container for drug to dissolve drug therewith. Such procedure is, however, complicated and time consuming. Moreover, there is a possibility of the drug in the container being contaminated because a hole for connection is formed on the container for drug in the open air.

In order to solve the above problem, there is proposed a fluid container as shown in Kohyo Tokkyo Koho No. 501129/1986 (which corresponds to U.S. Pat. No. 4,583,971).

As shown in FIG. 25, the fluid container has a capsule 102 encasing a vial 101, i.e. a drug container, and a flexible bag 103 containing a diluent and having a fluid outlet. The capsule 102 and bag 103 are connected to each other by a tube 104. In the tube 104, a hollow needle 105 is provided on the side of vial 101 while a breaking member 106 is provided on the side of flexible bag 103. The breaking member 106 closes a passage of the tube 104 and obstructs a flow of fluid.

In use, a cap 107 on the top of the capsule 102 is pushed with a finger to push down the vial 101. The needle 105 penetrates a rubber plug 108 of the vial 101 so that the flexible bag 103 and the vial 101 are connected to each other. Next the breaking member 106 in the tube 104 is bent with hands to open a passage of the tube 104 and to mix the drug and the diluent.

The above fluid container is improved in the point that mixing procedure is performed by communicating a drug container to a flexible bag containing a diluent. The mixing procedure is still troublesome since a passage for diluent must be opened by bending a breaking member 106 with the hands of the attendant after sticking a rubber plug 108 of a vial 101 with a needle 105. Moreover, when the bending of the breaking member 106 is incomplete, the diluent is hard to pass through the tube so that it takes a significant amount of time to carry out the dissolution of drug.

The present invention was made to solve the above drawbacks, and it is an object of the present invention to provide a fluid container for enabling sure and easy communication between a drug container and a diluent and which is capable of shortening the time required for the mixing of the drug and diluent after they are communicated.

SUMMARY OF THE INVENTION

In accordance with the present invention, there is provided a fluid container comprising;

a flexible bag containing a diluent therein and having a fluid passage with a closing film at its upper end;

a capsule connected to the flexible bag;

a drug container held in the capsule, an opening of the drug container being sealed hermetically with a stickable plug;

communicating means communicating the flexible bag with the drug container;

the communicating means comprising a double-edged hollow needle having a hub in the midway thereof, and controlling means for controlling the order of communication in such a manner that the plug of the drug container is stuck with one edge of the needle and after the closing film of the flexible bag is stuck with the other end of the needle.

In the fluid container of the present invention, the sticking order is so controlled by a controlling means that a plug of a drug container is first stuck and then closing film of a flexible bag is stuck. Accordingly, there is no problem that the closing film is firstly stuck and a diluent in the flexible bag leaks out into the capsule.

Further, the drug container and flexible bag are immediately communicated with each other after the plug of the drug container and the closing film of the flexible bag are stuck with a needle, since a hollow needle is used as a communicating means in the fluid container of the present invention. The movement of diluent is smooth, and is not disturbed by a mistake in operation or the like, since the container and bag are communicated to each other by means of a hollow needle. Therefore the mixing of drug and a diluent can be carried out in a short time.

BRIEF EXPLANATION OF THE DRAWINGS

Various other objects, features and attendant advantages of the present invention will be more fully appreciated as the same becomes better understood from the following detailed description when considered in connection with the accompanying drawings in which like reference characters designate like or corresponding parts throughout the several views and wherein:

FIG. 6 is a longitudinal sectional view of a fluid passage;

FIG. 7 is a longitudinal sectional view of a rubber stopper in the present invention;

DESCRIPTION OF THE PREFERRED EMBODIMENTS

Referring now to the accompanying drawings, a fluid container of the present invention is explained.

Figure 1:
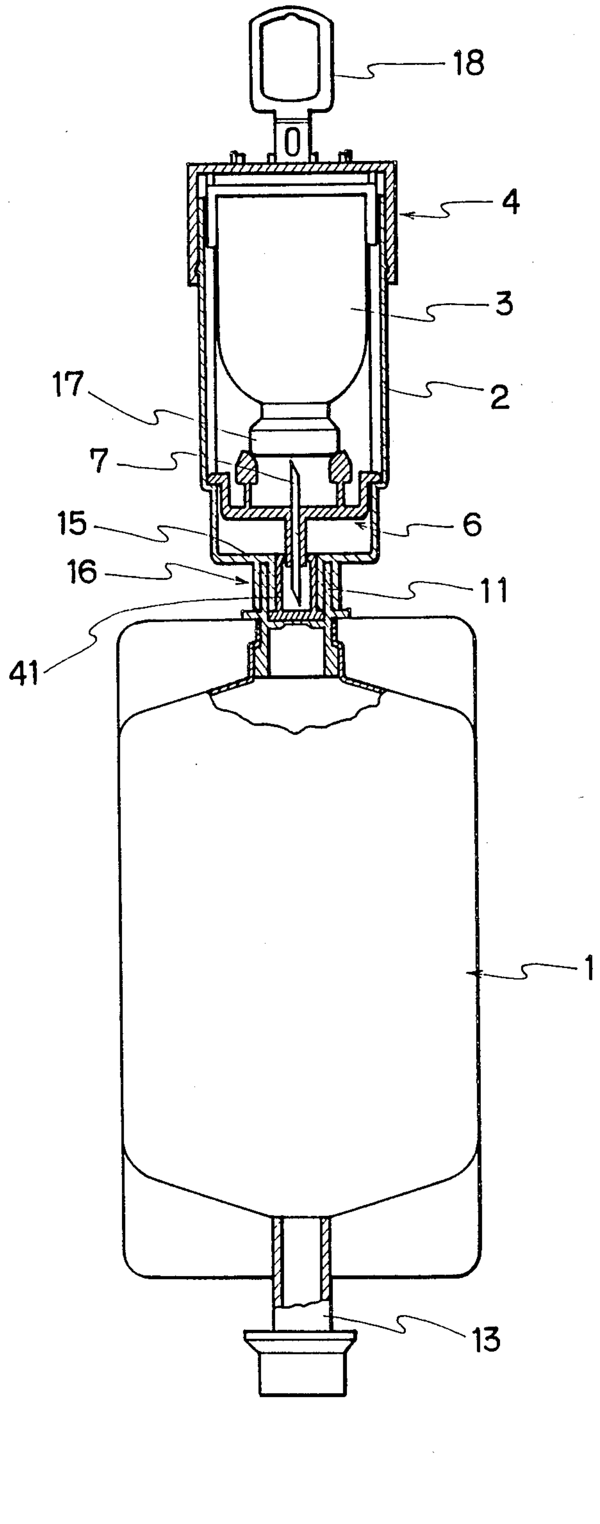
FIG. 1 is a partial sectional view of an embodiment of a fluid container of the present invention.
Figure 2:
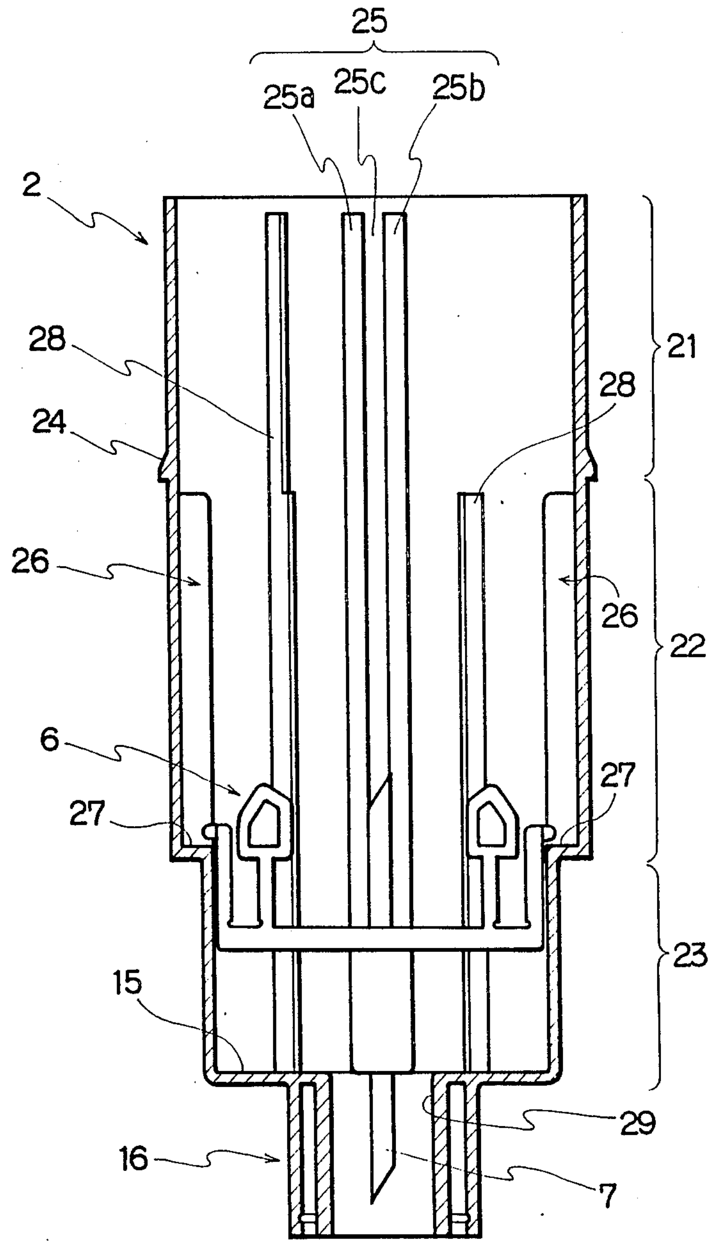
FIG. 2 is a longitudinal sectional view of a capsule in the present invention.
Figure 3:
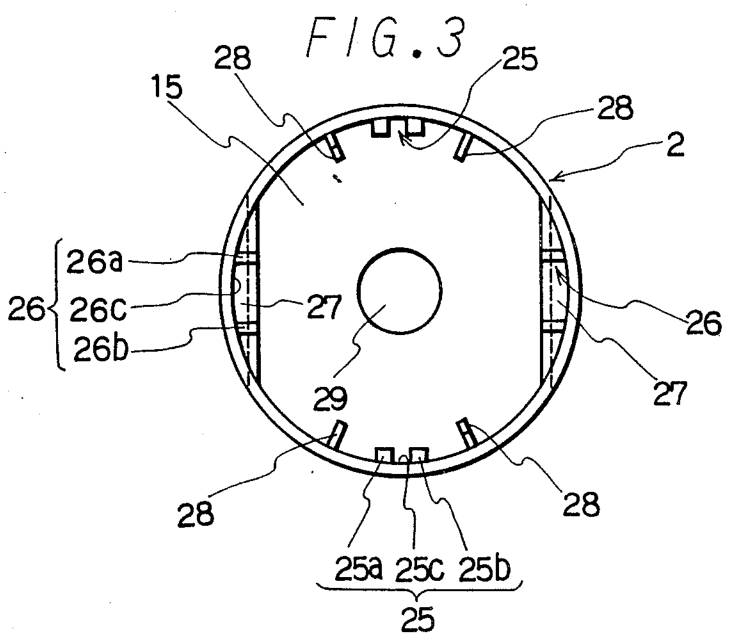
FIG. 3 is a plan view of the capsule.
Figure 4:
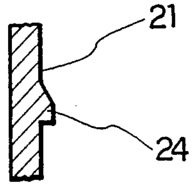
FIG. 4 is an enlarged view of an engaging projection of the capsule.

In FIG. 1, numeral 1 is a flexible bag (hereafter referred to as bag), numeral 2 is a capsule, numeral 3 is a vial used for a container of drug, and numeral 4 is a cap.

The bag 1 is a container for a diluent and is made of materials having great flexibility such as soft vinyl chloride resin, polyolefine resin and ethylene acetate copolymer. Among them, polyolefine resin can be preferably used since it has a superior drug resistance and evolution thereof into a diluent is little. The bag 1 has a fluid passage 11 at its upper end and a fluid outlet 13 at its lower end.

The capsule 2 is an approximately tubular container for containing a vial 3 and is made of materials such as polyolefine resin. The capsule 2 has an open upper end and a bottom 15 at its lower end. At the under surface of the bottom 15, a connecting portion 16 for connecting a fluid passage 11 of the bag 1 to the capsule is formed. Insertion of the fluid passage 11 into the connecting portion 16 gives a connection between the capsule 2 and the bag 1.

The vial 3 is encased in the capsule 2. The vial 3 is one of conventional type vials made of glass or plastics, and contains solid drug therein. The vial 3 is encased in the capsule 2 in such a manner that an opening 17 of the vial 3 point downward. The opening 17 is sealed up with a stickable rubber plug. In the capsule 2, a controlling means 6 having a needle 7 is placed between the opening 17 of the vial 3 and the bottom 15 of the capsule 2. The controlling means is used for controlling the sticking order of the needle 7, of which a detailed explanation is made after.

Figure 15:
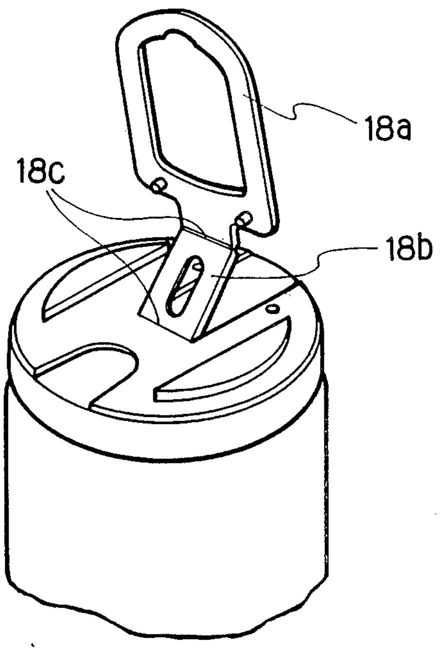
FIGS. 15 and 16 are perspective views showing an example of a hanger member in the present invention.
Figure 16:
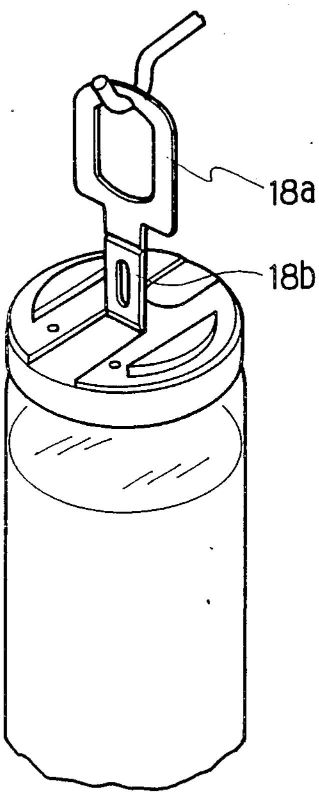

A cap 4 which serves to keep the vial 3 in a sterilized condition and push down the vial 3 is airtightly connected to the capsule. On the top surface of the cap 4, a hanger means 18 is provided. The hanger means 18 is used for suspending a fluid container and comprises, for examples, a ring 18*a* and a belt 18*b* as shown in FIGS. 15 and 16. The belt 18*b* can be folded at hinge portions 18*c*.

Next each element of the above fluid container is explained in detail.

FIGS. 2 to 5 show the details of the capsule 2. A substantially tubular capsule 2 consists of an upper portion 21, a middle portion 22 and a lower portion 23. The cap 4 is put on the upper portion 21. An annular engaging projection 24 is formed on the outer surface of the upper portion 21 at its lower end (see FIG. 4). A first guide 25 is formed inside the capsule 2 from the upper portion 21 to the lower portion 23. The first guide 25 consists of two wide longitudinal ribs 25*a*, 25*b* which define a sliding groove 25*c*. A pair of guides 25 are formed inside the capsule 2 symmetrically about a central axis of the capsule 2. The first guide 25 restrict rotational movement of a pressing member described below, and allows only movement of the pressing member in the axial direction.

Second guides 26 are formed on the inner surface of the middle portion 22 of the capsule 2 in the way in which the position thereof is shifted 90° away from that of first guides 25. The second guide 26 consists of two longitudinal ribs 26*a*, 26*b* which define a groove 26*c*. A pair of guides 26 are formed inside the capsule 2 symmetrically about a central axis of the capsule 2. A stopper 27 is formed at the lowest portion of the second guide 26. The second guide 26 serves to restrict rotational movement of the controlling means 6, while the stopper 27 serves to control the sticking order of the controlling means 6.

On the inner surface of the capsule 2, there are formed ribs 28 longitudinally which keep the vial 3 vertical in the capsule 2 and allow it move in an axial direction when being pressed by external force..

A hole 29 through which the needle 7 passes is made on the bottom of the capsule 2. A rubber stopper 41 discussed hereafter is inserted into the hole 29.

Figure 5:
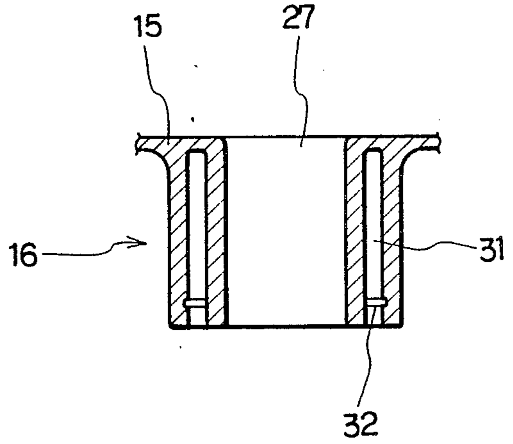
FIG. 5 is an enlarged sectional view of a connecting portion of the capsule.

A connecting portion 16 is formed on the under surface of the bottom 15 coaxially with the hole 29. The connecting portion 16 has a double-wall structure as shown in FIG. 5. An annular groove 31 formed between two walls is so designed as to receive the upper portion of the fluid passage 11. An engaging groove 32 is formed on the inner surface of the wall defining the groove 31.

The fluid passage 11 is a tubular body made of the same materials as bag 1, for example, polyolefine resin. The fluid passage 11 has an upper end portion 33 and a lower end portion 34 as shown in FIG. 6. At the periphery of the upper end portion 33, an engaging projection 35 and a flange 36 are formed. The engaging projection 35 is fitted in the engaging groove 32 to firmly connect the fluid passage 11 to the connecting portion 16. The lower end portion 34 is welded to the bag 1 by impulse sealer, hot mould, high-frequency welder, ultrasonic-generating apparatus and the like.

A closing film 38 is integrally formed with the fluid passage 11 inside a tubular body of the passage 11. At least a part of the closing film 38 is formed so as to be thin. The closing film 38 serves to keep the inside of the bag 1 liquidtight till it is stuck with a needle 7.

FIG. 7 shows a rubber stopper 41 which is a rubber tubular body having a bottom 42 to present leakage of a diluent into the capsule 2. An annular rib 44 is formed on the inner surface of upper end portion of a tubular body 43. The rib 44 tightly contacts with outer surface of a hub of the needle 7 described hereinafter and corresponds to "sealing means" stated in claims. A conical notch 45 is formed in the center of inner surface of the bottom 42. The conical notch 45 serves to avoid an accident whereby rubber of the bottom 42 is cut off by the edge of the needle 7 when sticking the needle 7 into the bottom 42 and the needle 7 is stopped up with the cut-off rubber. The bottom 42 is so designed as to contact with a surface of the closing film 38 on the side of the capsule 2 when the rubber stopper 41 is inserted into the fluid passage 11 on the side of the capsule 2. The bottom 42 corresponds to "elastic means" stated in claims.

Figure 8:
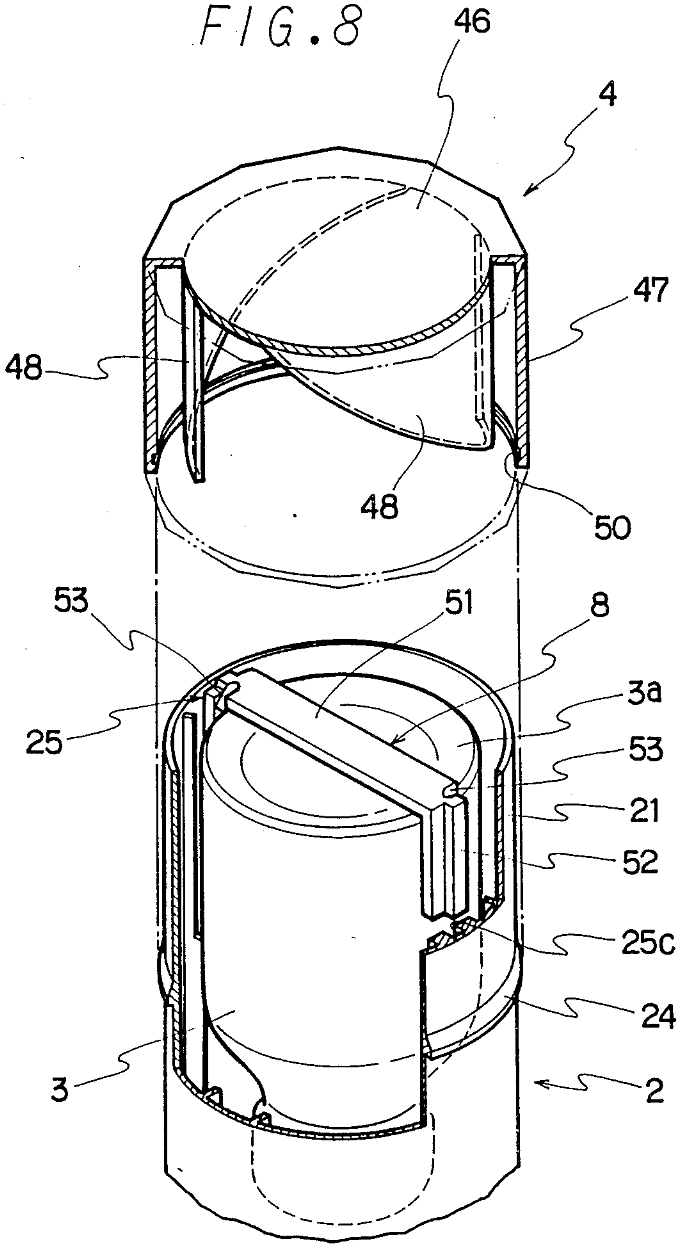
FIG. 8 is a partially cut-away perspective view explaining a pushing-down mechanism used in the present invention.

A mechanism for pushing down a vial with the use of a cap 4 is now explained based on FIG. 8.

The cap 4 is a tubular body having a top flat portion 46 and a tubular sidewall 47. In FIG. 8, the hanger means to be provided on the upper surface of the top flat portion 46 is not shown. An annular engaging groove 50 is formed on the inner surface of the lower end portion of the sidewall 47. When the cap 4 is put on the upper portion 21 of the capsule 2, the projection 24 is set in the groove 50. In this state, the cap 4 is rotatable about the capsule 2 while it cannot move in an axial direction. Two cams 48 are formed on the under surface of the top flat portion 46 of the cap 4. Each cam 48 is an arc-like plate extending over about 140°. The pair of cams are symmetrically provided with respect to an axis of the cap 4. The height of each cam 48 linearly varies. The vial 3 is encased in the capsule 2. The bottom 3a of the vial 3 on which a pressing member is put is positioned at an upper opening of the capsule 2.

The pressing member 8 is a cramp-shaped member having a beam 51 and guide rods 52 extending downwardly from the end of the beam 51. A cam-following slope 53 is formed at the upper end of each guide rod 52. The guide rod 52 is put in a groove 25c of a guide 25 formed on the inner surface of the capsule. The guide rod 52 can go up and down in the axial direction but cannot rotate about the axis of the capsule 2.

When the cap 4 is rotated with the cap 4 engaged with the upper portion 21 of the capsule 2, the cam 48 contacts the cam-following slope 53 of the pressing member 8 and pushes down the vial 3 in the capsule 2.

Next a mechanism for controlling the sticking order with the help of a controlling means 6 will be explained based on FIGS. 9 to 11.

Figure 9:
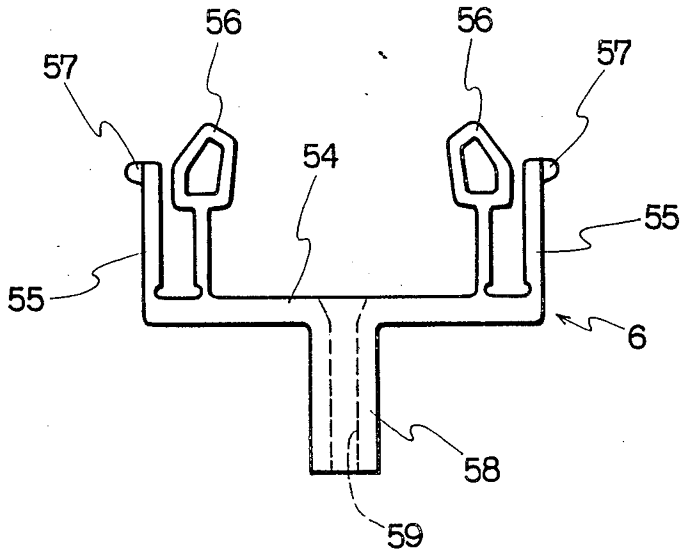
FIG. 9 is a front view of controlling means used in the present invention.
Figure 10:
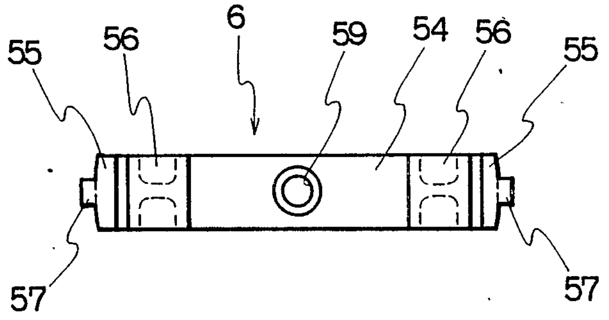
FIG. 10 is a plan view of the controlling means.
Figure 11:
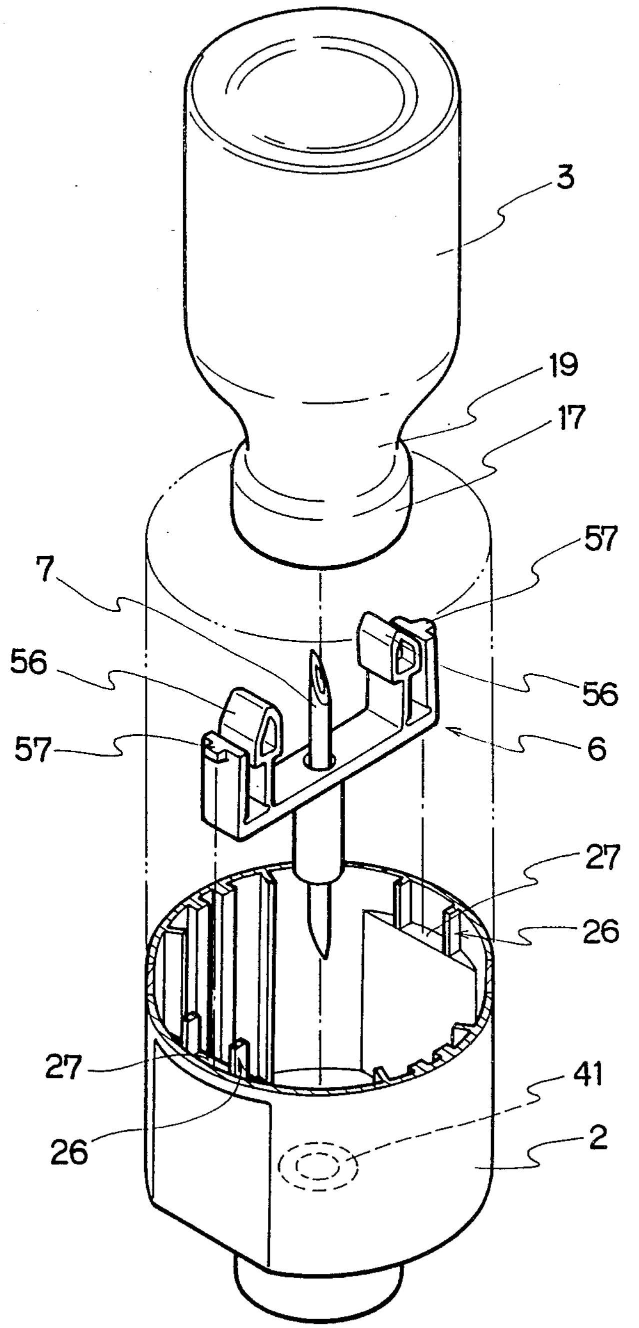
FIG. 11 is a partially cut-away perspective view explaining a mechanism for controlling the sticking order.

FIGS. 9 to 11 show controlling means 6 having an arm 54, engaging portions 55 extending upwardly from both ends of the arm 54, and pressing portions 56 standing inside the engaging portions 55. The controlling means 6 is made of flexible synthetic resin such as polypropylene. An engaging projection 57 is formed laterally and outwardly at a tip portion of the engaging portion 55. A head of the pressing portion 56 is so shaped as to engage with a neck 19 of the vial 3. The distance between two pressing portions 56 is a little smaller than the outer diameter of an opening of the vial 3, and is a little larger than the outer diameter of the neck 19. There is a clearance between the pressing portion 56 and engaging portion 55 which allows the engaging portion 55 to bend inwardly. In the center of the arm 54 a hub 58 of the needle 7 is integrally formed with the arm 54. A cannula of the needle 7 is inserted into a hole 59 of the hub 58 and fixed to the hub 58.

The controlling means 6 is put in the capsule 2 as shown in FIG. 11, and installed in the capsule 2 in so that the engaging projection 57 contacts with the stopper 27 of the capsule 2. The controlling means 6 and needle 7 correspond to "communicating means" stated in claims.

The following drugs are usable as a drug to be contained in a vial in the present invention.

As antibiotics, there can be used cephem antibiotics such as cefazolin sodium, ceftizoxime sodium, cefotiam dihydrochloride, cefmenoxime hemihydrochloride, cefacetrile sodium, cefamandole sodium, cefaloridine, cefotaxime sodium, cefotetan sodium, cefoperazone sodium, cefsulodin sodium, ceftezole sodium, cefpiramide sodium, cefmetazole sodium, or cefuroxime sodium; or penicillin antibiotics such as ampicillin sodium, carbenicillin disodium, sulbenicillin disodium, or ticarcillin sodium. As an antitumor agent, mitomycin C, fluorouracil, tegafur, cytarabine, etc. can be used. As an antiulcer agent, famotidine, ranitidine hydrochloride, cimetidine, etc. can be used.

Saline, 5% dextrose solution, distilled water for solution or various kinds of solution containing electrolytes can be used as a diluent contained in the bag 1.

The communicating operation of the fluid container assembled in the manner as stated above will now be explained based on FIGS. 12 to 14.

Figures 12, 13, 14:
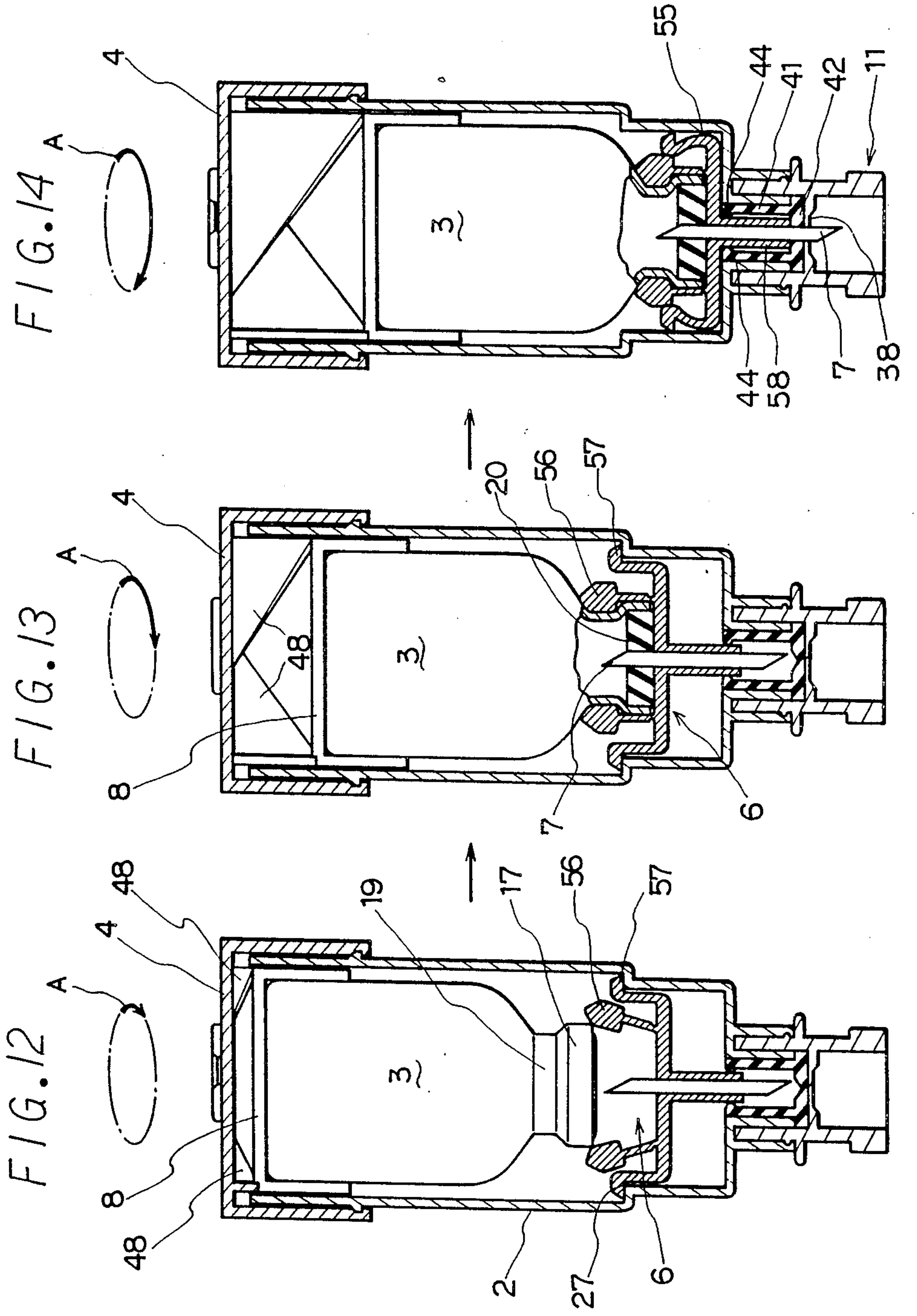
FIGS. 12 to 14 are sectional views explaining the sticking process of the embodiment of FIG. 1.

When the cap 4 is rotated in the direction shown by an arrow A in FIG. 12, the vial 3 goes down because the cam 48 pushes down the pressing member 8. Upon the descent of the vial 3, the opening 17 of the vial 3 pushes and bends the pressing portion 56 of the controlling means 6 outwardly. In that case, the engaging projection 57 does not come off from the stopper 27 since the distance between the pressing portion 56 and the engaging projection 57 is narrow and therefore the engaging projection 57 touches the pressing portion 56 even if the engaging portion 57 tries to come off from the stopper 27. Accordingly, the descent of the vial 3 does not cause the controlling means to go down.

Further rotation of the cap 4 in the direction shown by an arrow A would make the vial 3 go down until the opening 17 thereof is sandwiched between two pressing portions, and the rubber plug 20 in the opening 17 is stuck with an upper edge of the needle 7 as shown in FIG. 13.

Since the distance between the pressing portion 56 and the engaging projection 57 is narrow until the sticking with the needle is completed as stated above, the controlling means 6 does not go down. The pressing portion 56 returns to its original position, i.e. upright position, the moment the sticking is completed, whereby generating sufficient a clearance between the engaging projection 57 and the pressing portion 56 (see FIG. 13). This sufficient clearance enables the controlling means 6 to come off from the stopper 27 and go down.

Still further rotation of the cap 4 in the direction shown by an arrow A causes the vial 3 to go down. With the descent of the vial 3, the controlling means 6 goes down since the engaging portion 55 is bent inwardly (see FIG. 14). Then, a lower edge of the needle 7 sticks the bottom 42 of the rubber stopper 41 and closing film 38 of the fluid passage 11 occurs successively, so that the inside of the vial 3 and inside of the bag 1 communicates with each other through the needle 7. Diluent in the bag 1 does not leak into the capsule 2 since the rubber plug 20 of the vial 3 in the capsule 2 is firstly stuck and thereafter the closing film 38 of the bag 1 is stuck. Since the annular rib 44 of the rubber stopper 41 closely or liquidtightly contacts with outer surface of the hub 58 from the beginning, diluent does not leak even at an early stage of sticking of closing film 38 with the needle 7.

When the bag 1 is pressed or squeezed after the vial 3 and bag 1 communicate with each other in the manner described above, a part of diluent moves into the vial 3 and dissolves the drug in the vial 3. Fluid in the vial 3 returns to the bag 1 when the bag 1 is pressed or squeezed again. An infusion tube and the like is connected to a fluid outlet 13 of the bag 1 and returned fluid is used for dripping.

Next, another embodiment of the present invention is explained based on FIGS. 17 to 21. Elements or assemblies other than those explained hereinafter are substantially the same as those in the above-mentioned embodiment.

Figure 17:
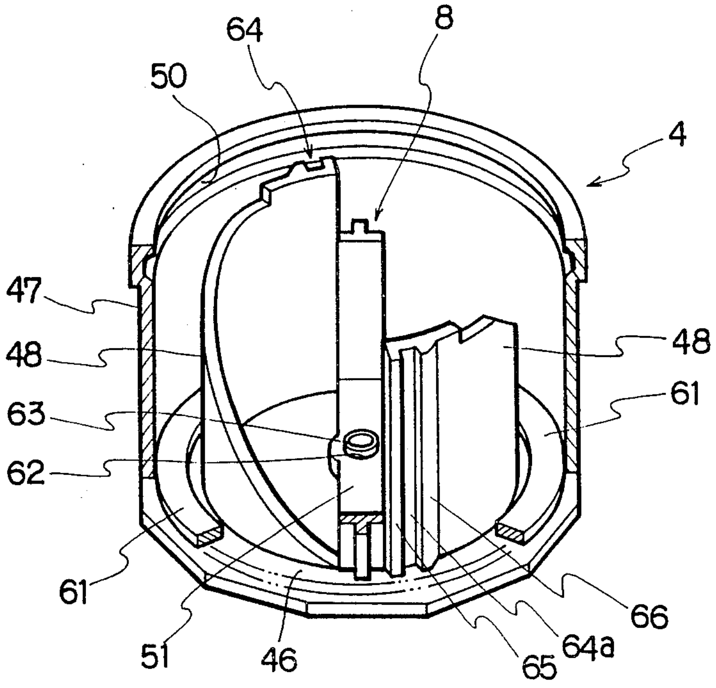
FIG. 17 is a partially cut-away perspective view showing a cap of a fluid container according to another embodiment of the present invention.

FIG. 17 is a partially cut-away explanatory view of a upside-down cap 4. Between a sidewall 47 of the cap 4 and a cam 48, a ring-like rubber packing 61 is placed in the way in which the packing 61 closely contacts with a top flat portion of the cap 4. The use of packing 61 improves the airtightness between an upper end surface of a capsule 2 and an inner surface of the cap 4.

A pressing member 8 in FIG. 17 has a hole 62 in the center of a beam 51. On the other hand, a projection 63 is formed in the center of inner surface of a top flat portion 46. By the engagement between the hole 62 and projection 63, the pressing member 8 is securely held and is not easily disengaged from the cap 4. That is, in assemblying a fluid container of the present invention, the pressing member 8 does not accidentally come off from the cap 4 if the hole 62 of the pressing member 8 is engaged with the projection 63, whereby assemblying work becomes easy. When the cap 4 is rotated to push down the pressing member 8 with a cam 48, the engagement between the hole 62 and projection 63 is easily released.

Figure 18:
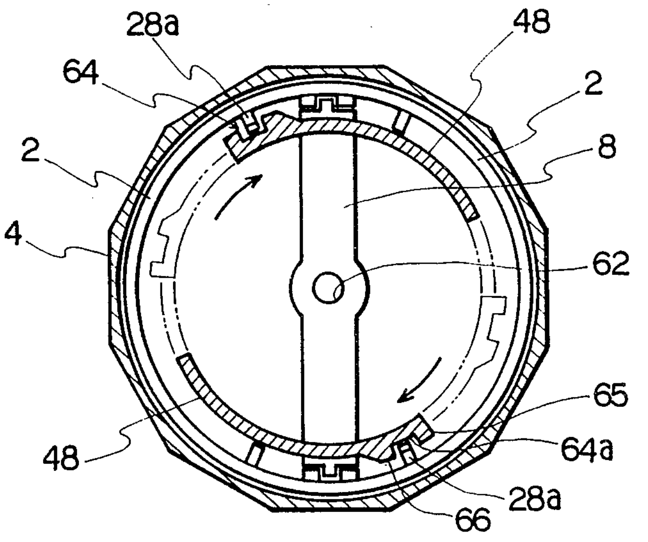
FIG. 18 is a horizontal sectional view showing a state wherein the cap of FIG. 17 is put on a capsule.

A cam 48 of the cap 4 shown in FIGS. 17 and 18 has a stopper 64 at its end portion. The stopper 64 consists of ribs 65, 66 defining a groove **64*a* therebetween. The rib 66 has a slope portion. The capsule 2 has, as shown in FIGS. 18 to 19, an extended rib 28*a* extending from a rip 28 to the upper portion 21 of the capsule 2**.

The stopper 64 is so designed as to engage with the extended rib **28*a* when the cap 4 is put on capsule 2 and is rotated until the vial 3 is pushed down to its end position as shown in FIG. 28. The rib 66 can climb over the extended rib 28*a* with little resistance since the rib 66 has a slope portion. Once the extended rib 28*a* is in place in the groove 64*a*, however, rotation of the cap 4 is prevented since ribs 65, 66 touch the extended rib 28*a***.

Thanks to the formation of stopper 64, the fluid container according to the present embodiment can prevent the vial 3 from being pushed upwardly due to the resilience of the rubber plug 20 when the plug 20 is sticked with the needle 7. Accordingly the needle 7 can surely and perfectly stick the rubber plug 20.

Figure 19:
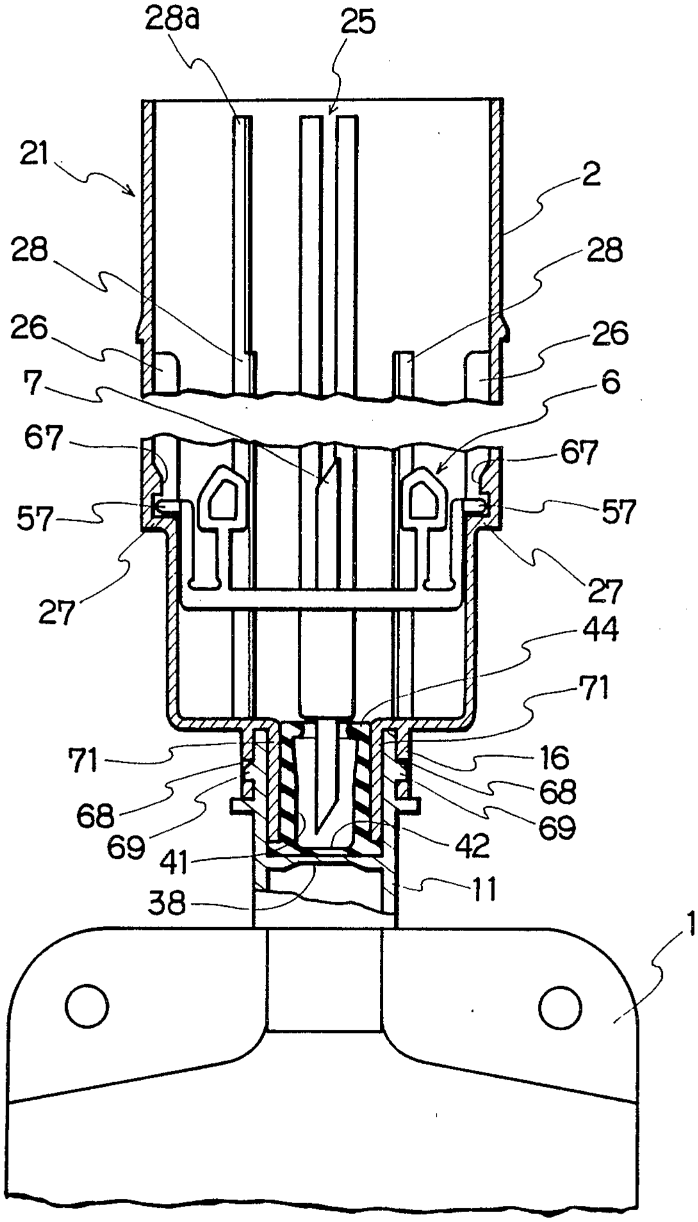
FIG. 19 is a longitudinal sectional view of a capsule of the fluid container of another embodiment of FIG. 17.

In the present embodiment there is formed a projection 67 above the stopper 27 in the capsule 2, i.e. below the guide 26, as shown in FIG. 19. The projection 67 is so positioned as to be above the engaging projection 57 and as to contact therewith, when the controlling means 6 is inserted into the capsule 2 in the way in which the projection 57 is on the stopper 27. The projection 67 prevents free movement of the controlling means 6 during assembly work and can make such work easy to perform.

Figure 20:
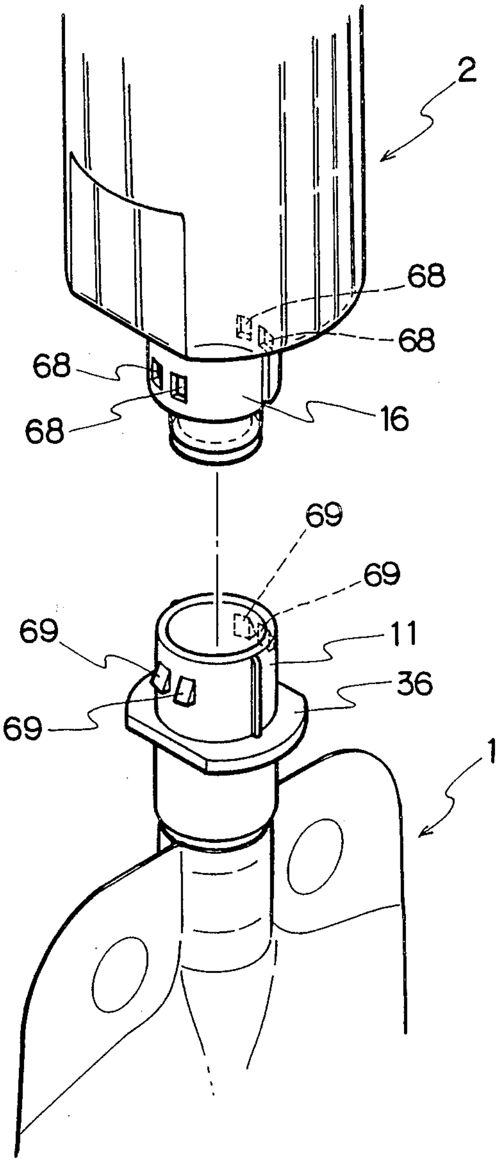
FIG. 20 is a perspective view showing a connecting mechanism of a capsule and a bag of fluid container according to another embodiment.

FIG. 20 shows a combination structure between the capsule 2 and bag 1 of the present invention. Connecting holes 68 made on a connecting portion 16 of the capsule 2 and connecting projections 69 formed on the outer surface of fluid passage 11 connected to the bag 1 engage with each other. FIG. 19 shows a state wherein the capsule 2 is connected to the bag 1 by means of above-mentioned engagement between holes 68 and projections 69. Such engagement is very firm and is not easily released.

A rubber stopper 41 of the present embodiment is inserted inside the inner wall 71 of the connecting portion 16 as shown in FIG. 19. All of the bottom 42 of the rubber stopper 41 is made so as to be thin, and accordingly does not have a notch as a rubber stopper 41 shown in FIG. 7. The sticking resistance of the needle 7 is reduced as well as the rubber stopper 41 because the whole bottom 42 is made so as to be thin.

Figure 21:
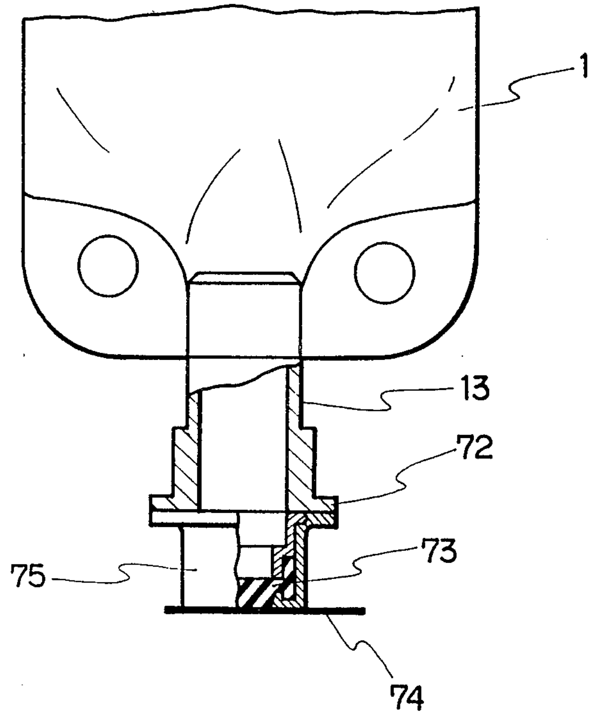
FIG. 21 is a partially sectional view showing a fluid outlet of a bag of the fluid container according to another embodiment.

FIG. 21 shows a fluid outlet 13 of the present embodiment. A flange 72 is formed at the bottom end of the fluid outlet 13. A cap 75 into which a rubber plug 73 is inserted is connected to the flange 72. A seal 74 is adhered to the bottom surface of the rubber plug 73. A plastic sheet can be preferably used for materials of the seal 74. The seal 74 is adhered to the rubber plug 73 till the fluid container is used. The use of seal 74 can prevent contamination of the surface of the rubber plug 73.

In the above-mentioned embodiment, the sticking order of the needle 7 is controlled as in the embodiment shown in FIGS. 1 to 16, and leakage of diluent is prevented. Further, mixing of drug and diluent can be carried out in a short time and easily.

Next, a still another embodiment of the present invention is explained.

Figure 22:
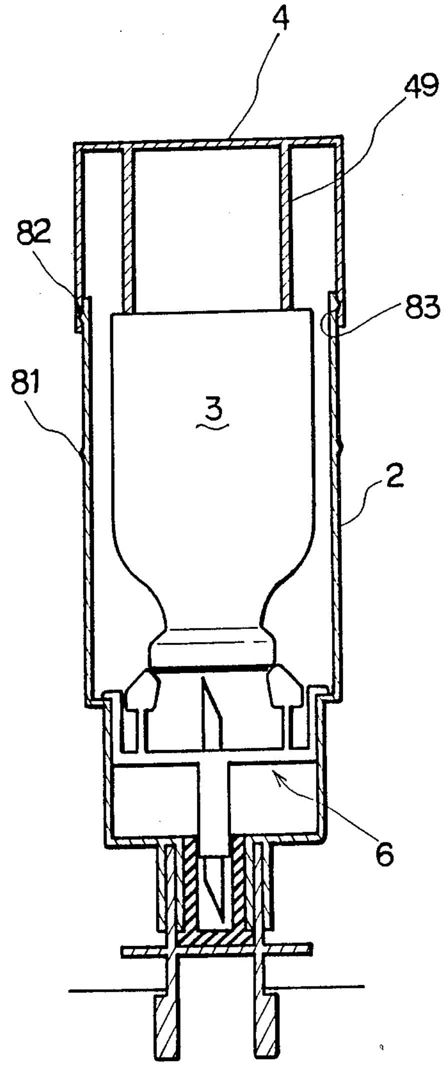
FIGS. 22 and 23 are sectional views showing a sticking operation of a fluid container according to still another embodiment of the present invention.
Figure 23:
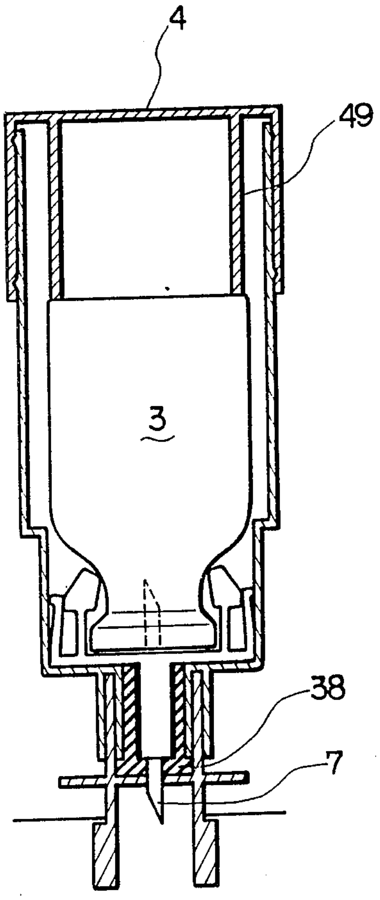

An embodiment of FIGS. 22 and 23 has a tubular pusher 49 inside the cap 4. The end of the pusher 49 directly contacts with a bottom of the vial 3. Engaging projections 81, 82 are formed in the middle and on the upper end of the outer surface of the capsule 2, while an engaging recess 83 is formed on the inner surface of the cap 4.

In the present embodiment, the vial 3 can go down by directly pushing down the cap 4 with a hand as shown in FIG. 23, thereby enabling the needle 7 to stick a rubber plug 20 of the vial 3 and a closing film 38 of the bag 1. In that case, the attachment of the controlling means 6 enables controlling of the sticking order in the well as embodiments described above. When the engaging recess 83 of the cap 4 is engaged with upper end projection 82 of the capsule 2, the cap 4 is not easily pulled out from the capsule 2. When the recess 83 engages with a middle projection 81, completion of pushing down of the cap 4 can occur.

The present invention includes another embodiment using a deformable and flexible member attached to a top portion of a side wall of a capsule 2 wherein a vial is pushed down by fingers of the user with bending of the flexible member, and still another embodiment using a cap having a central flat portion and plurality of wrinkles around the flat portion.

Figure 24:
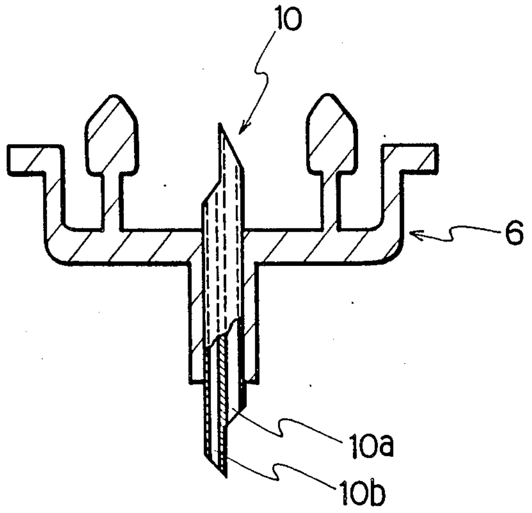
FIG. 24 is a partial sectional view showing another example of a needle used in a fluid container of the present invention.
Figure 25:
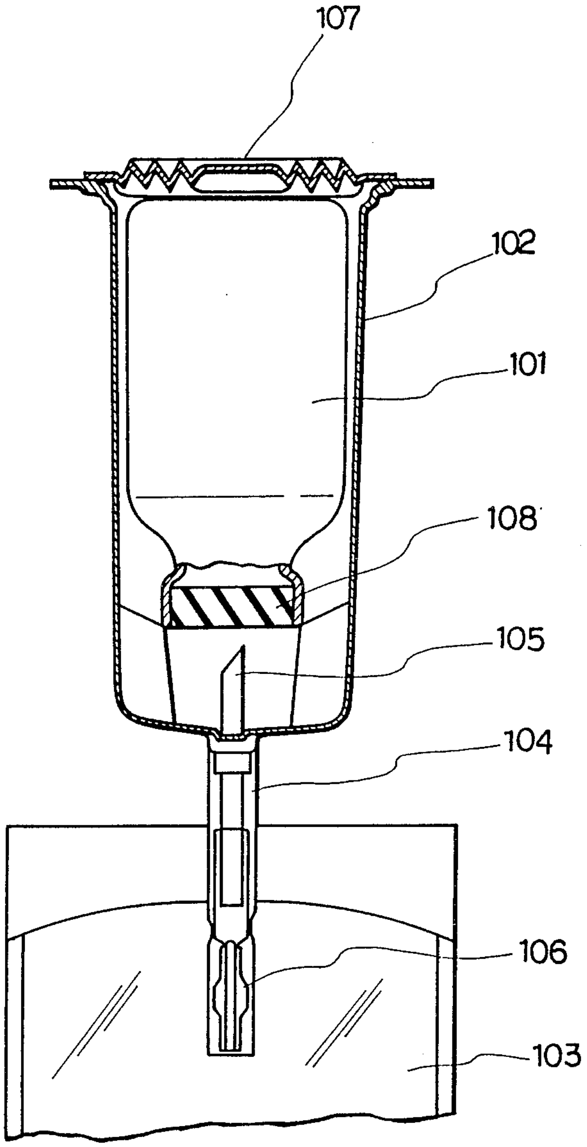
F I G. 25 (PRIOR ART)
FIG. 25 is a partial sectional front view of a conventional fluid container.

Though needles 7 each having one liquid passage are employed in the embodiments described above, there can instead be used a needle 10 having two liquid passages in the present invention. FIG. 24 shows an example of such needle having two liquid passages **10*a*, 10*b***.

The needle 10 has an advantage in that the passage speed of liquid is high since air passes through one passage and liquid passes through the other passage. Accordingly, the mixing of drug and diluent can be carried out in a shorter period of time.

Though the present invention is explained based on some specific embodiments, various kinds of modifications can be employed in the present invention without departing from a scope of the present invention.

According to a fluid container of the present invention, the sticking order is so controlled by a controlling means that a plug of a drug container is first stuck and then a closing film of a flexible bag is stuck. Accordingly, there is no problem that the closing film is first stuck and a diluent in the flexible bag leaks out into the capsule.

The movement of diluent is smooth, and is not disturbed by a mistake in operation of the like, since the container and bag are communicated with each other by means of a hollow needle. Therefore the mixing of a drug and a diluent can be carried out in a short period of time.

What is claimed is:

1. A fluid container, comprising:

a flexible bag containing a diluent therein and having a fluid passage with a closing film at an upper end thereof;

a capsule connected to the flexible bag;

a drug container held in the capsule, an opening of the drug container being sealed hermetically with a stickable plug;

communication means communicating the flexible bag with the drug container wherein the communicating means comprises an elongated hollow needle having two pointed ends and having a hub midway thereof, and controlling means for controlling the order of communication in such a manner that the plug of the drug container is stuck with one end of the needle and thereafter the closing film of the flexible bag is stuck with the other end of the needle.

2. The fluid container of claim 1, wherein the drug container comprises a vial.

3. The fluid container of claim 2, wherein the controlling means is attached to the hub of the needle and engages with a stopper formed on an inner wall of the capsule, the controlling means being so designed as to come off from the stopper and enable the needle to move downwardly when the vial is moved downwardly to such a position that a plug of the vial is stuck with the needle.

4. The fluid container in claim 2, wherein the flexible bag has a fluid outlet at a lowest end portion thereof.

5. The fluid container of claim 3, wherein an elastic body is placed on the surface of the closing film of the flexible bag on the side of the capsule.

6. The fluid container of claim 3, wherein the needle is slidably and liquidtightly sealed with a rubber-like elastic sealing means in the fluid passage.

7. The fluid container of claim 3, wherein a cap for lowering the vial is airtightly put on the capsule.

8. The fluid container of claim 7, wherein the cap has a hanger member at its top surface.

9. The fluid container of claim 7, wherein the cap is so designed as to enable downward movement of the vial when the cap is pushed down.

10. The fluid container of claim 7, wherein the cap is so designed as to enable downward movement of the vial when the cap is rotated.

11. The fluid container of claim 3, wherein the capsule has an opening at its upper end, a flexible member is attached to the opening, and the flexible member is substantially deformable in order to enable the vial to go down by pushing down the flexible member with a finger.

12. The fluid container of claim 11, wherein the flexible member has a central flat portion and plural wrinkles around the flat portion.

13. The fluid container of claim 1, wherein the needle has one liquid passage.

14. The fluid container of claim 1, wherein the needle has two liquid passages.

* * * * *